United States Patent [19]

Fujishima et al.

[11] Patent Number: 4,767,713
[45] Date of Patent: * Aug. 30, 1988

[54] PURE CULTURE OF *BREVIBACTERIUM ACETYLICUM* AT-6-7, ATCC 39311

[75] Inventors: Tetsuro Fujishima; Shinji Sakata, both of Choshi, Japan

[73] Assignee: Yamasa Shoyu Kabushiki Kaisha, Chiba, Japan

[*] Notice: The portion of the term of this patent subsequent to Jun. 10, 2003 has been disclaimed.

[21] Appl. No.: 834,360

[22] Filed: Feb. 28, 1986

Related U.S. Application Data

[62] Division of Ser. No. 479,979, Mar. 29, 1983, Pat. No. 4,594,321.

[30] Foreign Application Priority Data

Apr. 1, 1982 [JP] Japan .................................. 57-55078

[51] Int. Cl.$^4$ .................. C12N 1/20; C12N 9/12; C12R 1/13
[52] U.S. Cl. .................................. 435/253; 435/194; 435/840
[58] Field of Search .................. 435/85, 87, 88, 89, 435/193, 194, 253, 840

[56] References Cited

U.S. PATENT DOCUMENTS

| | | | |
|---|---|---|---|
| 4,458,016 | 7/1984 | Yamanaka et al. | 435/85 |
| 4,594,321 | 6/1986 | Fujishima et al. | 435/840 X |
| 4,614,719 | 9/1986 | Fujishima et al. | 435/193 X |

*Primary Examiner*—Thomas G. Wiseman
*Assistant Examiner*—Jayme A. Huleatt
*Attorney, Agent, or Firm*—Wenderoth, Lind & Ponack

[57] ABSTRACT

The invention is directed to a microbially pure culture of *Brevibacterium acetylicum* AT-6-7, ATCC 39311 or a mutant thereof which has nucleoside phosphorylase activity.

3 Claims, No Drawings

PURE CULTURE OF *BREVIBACTERIUM ACETYLICUM* AT-6-7, ATCC 39311

BACKGROUND OF THE INVENTION

This invention relates to an enzymatic process for producing 3'-deoxyguanosine.

3'-Deoxyguanosine is a compound presently attracting attention which not only exhibits radiation sensitizing action in therapy of cancers but also has an action to enhance the effect of various anticancer agents when employed in combination therewith (see Japanese Laid-open Publication No. 35516/1982).

In the prior art, as the method for preparation of 3'-deoxyguanosine, is known the method in which a chloromercuri of 2-acetamidohypoxanthine is condensed with 2,5-di-O-benzoyl-3-deoxy-D-ribofuranosyl bromide [The Journal of Organic Chemistry, 30, 2851 (1965)]. However, this method is believed to involve various drawbacks in commercial production such as, for example, difficult availability of the starting material 3-deoxyribose, formation of isomers during the condensation reaction, use of a harmful mercuric salt, and others.

SUMMARY OF THE INVENTION

The present inventors have made various investigations in order to overcome these drawbacks of the prior art and consequently found that 3'-deoxyguanosine can be formed by causing a guanine derivative to react with a 3'-deoxyribose donor in the presence of a nucleoside phosphorylase source. The present invention has been accomplished based on such a finding.

The present invention provides a process for producing 3'-deoxyguanosine, which comprises causing a guanine derivative represented by the formula [I]:

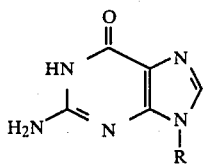

wherein R designates a hydrogen atom or a ribose-1-yl group, a 2-deoxyribose-1-ly group or a monophosphate, a diphosphate or a triphosphate thereof, to react with a 3-deoxyribose donor in the presence of a nucleoside phosphorylase source to obtain 3'-deoxyguanosine.

DETAILED DESCRIPTION OF THE INVENTION

The present invention is to be described in detail below.

Guanine derivative

As the starting guanine derivatives, there may be employed one or more of the compounds included within the aforementioned definition. More specifically, illustrative of these compounds are guanine (Gua), guanosine (Guo) or 2'-deoxyguanosine (2'-dGuo) or monophosphates, diphosphates or triphosphates thereof. The above nucleotide may have a phosphoryl group at any position of hydroxyl groups in the sugar residue. Typical examples of these nucleotides may include guanosine-5'-mcnophosphate (GMP), guanosine-3'-monophosphate, guanosine-2'-monophasphate, guanosine-5'-diphosphate (GDP), guanosine-5'-triphosphate (GTP), 2'-deoxyguanosine-5'-monophosphate (2'-dGMP), 2'-deoxyguanosine-3'-monophosphate, 2'-deoxyguanosine-5'-diphosphate (2'-dGDP), 2'-deoxyguanosine-5'-triphosphate (2'-dGTP) and the like, which may be either in free acid form or in an appropriate salt form such as sodium salt.

3-Deoxyribose donor

As the other starting material, a 3-deoxyribose donor, there may be employed any compounds which are capable of enzymatically introducing 3-deoxyribose moiety to the 9-position of the guanine moiety of the compound of formula [I] through direct glycosylation or transglycosylation. Typical examples include one or more of 3'-deoxyadenosine (3'-dAdo; cordycepin), 3'-deoxyinosine (3'-dIno), or monophosphates, diphosphates or triphosphates thereof, or 3-deoxyribose-1monophosphate. The above phosphates may have phosphoryl group at any position of hydroxyl group in 3-deoxyribose, and may also be either in free acid form or in a salt form. Illustrative of these nucleotides are 3'-deoxyadenosine-5'-monophosphate (3'-dAMP), 3'-deoxyinosine-5'-monophosphate (3'-dIMP) or 3-deoxyribose-1 -phosphate.

Nucleoside phosphorylase source

The nucleoside phosphorylase which is in the nucleoside phosphorylase source in the reaction of the present invention refers comprehensively to a single enzyme or a plurality of enzymes capable of providing 3'-deoxyguanosine by causing the guanine derivative to react with the 3-deoxyribose donor in the presence of a phosphoric acid ion donor. Accordingly, in the present invention, the term "nucleoside phosphorylase source" includes the enzymes of the phosphorylase type such as purine nucleoside phosphorylase, pyrimidine nucleoside phosphorylase, etc., which can be used in combination with enzymes such as nucleoside-N-glycosyl transferase, nucleosidase, nucleotidase, phosphatase and others, which may possibly participate in the reaction of the present invention. The nucleoside phosphorylase source refers comprehensively to a material containing such enzymes in any desired form, which is not limited in its origin or source. That is, any enzyme material may be applicable so long as it can accomplish the object of the present invention, irrespective of whether it may be derived from microorganisms or from animals, or whether it may be prepared in any form. In particular, a nucleoside phosphorylase source of a microorganism origin, namely a nucleoside phosphorylase source in the form of a culture, a mass of intact cells or a modification of cells of a microorganism, is preferred.

Preferred nucleoside phosphorylase sources of microorganism origin are those based on microorganisms which belong to genera Pseudomonas (hereinafter referred to as Ps.), Brevibacterium (hereinafter referred to as Br.) and Achromobacter (hereinafter referred to as Ach.).

Typical strains of such microorganisms are:
Ps. desmolytica J-4-2:
  FERM P-6307, ATCC 39310
Br. acetylicum AT-6-7: .
  FERM P-6305, ATCC 39311
Ach. eurydice BE-3-3:
  FERM P-6304, ATCC 39312

Typical strains among these are the first three strains, namely J-4 −2 strain isolated from the soil in Nishiashikajima-Cho, Choshi-Shi, Chiba-Ken, Japan; the AT-6-7 strain isolated from the sand in the baseball ground of Koshien, Nishinomiya-Shi, Hyogo-Ken, Japan; and the BE-3-3 strain isolated from the soil in AraoiCho, Choshi-Shi, Chiba-Ken, Japan. The bacteriological properties of these strains are set forth below.

1. J-4-2 strain

A. Morphology
(1) Form and size of cells: rod-shaped, 0.7–0.8×2.0–3.0 μm;
(2) Motility, occurrence of flagella: motile with polar flagella;
(3) Formation of spores: none
(4) Gram staining: negative B. Growth on various culture media
(1) Boulillon-agar plate culture (28° C., 48 hours)
  ① Form of colony: circular
  ② Raising of colony surface: raised or umbonate
  ③ Size: 2–4 mm
  ④ Color tone: gray to buff when wet
(2) Bouillon-agar slant culture (28° C., 48 hours)
  ① Growth: good
  ② Form of growth: filliform and slightly spreading
  ③ Formation of pigment: not clear
(3) Bouillon liquid culture (28° C., 72 hours)
  Growth: no membrane formation, turbid throughout the entire liquid, sediment slightly formed.
(4) Bouillon-gelatin stab culture (20° C., 6 days): not liquefied
(5) Litmus-milk culture medium (28° C., 4 days): not changed.

C. Physiological properties
(1) Reduction of a nitrate (28° C., 5 days): reductive
(2) Formation of hydrogen sulfide (28° C., 5 days): formed
(3) Hydrolysis of starch: not hydrolyzed
(4) Catalase: positive
(5) Indole formation: negative
(6) Ammonia formation from peptone and arginine: negative
(7) Methyl red test: negative
(8) V-P test: positive
(9) Attitude to oxygen: aerobic
(10) O-F test (by the Hugh Leifson method): O type (Oxidation)
(11) Acid formation from sugars
  positive: glucose, mannose, fructose, maltose, saccharose, trehalose and mannitol;
  negative: arabinose, xylose, galactose, lactose, sorbitol, inositol and glycerine
(12) Growth pH range: pH 6.0–9.0
(13) Optimum growth temperature: 25°–35° C.

2. AT-6-7 strain

A. Morphology
(1) Form and size of cells: short rod-shaped, 0.8–1.0×1.0–1.2 μm;
(2) Formation of spores: none
(3) Gram staining: positive B. Growth on various culture media
(1) Bouillon-agar plate culture (28° C., 48 hours)
  ① Form of colony: circular
  ② Raising of colony surface: flat, smooth
  ③ Size: 2–4 mm
  ④ Color tone: yellow to peach-yellow
(2) Bouillon-agar slant culture (28° C., 48 hours)
  ① Growth: good
  ② Form of growth: echinulate
(3) Bouillon liquid culture (28° C., 48 hours)
  Growth: formation of ring on the surface, sediment slightly formed.
(4) Bouillon-gelatin stab culture (20° C., 6 days): liquefied in stratiform
(5) Litmus-milk culture medium (28° C., 4 days): slightly coagulated, peptonization also observed C. Physiological properties
(1) Reduction of a nitrate (28° C., 5 days): no reductivity
(2) Formation of hydrogen sulfide (28° C., 5 days): not formed
(3) Hydrolysis of starch: hydrolyzed
(4) Catalase: positive
(5) Indole formation: not forced
(6) Ammonia formation from peptone and arginine: negative
(7) Methyl red test: negative
(8) V-P test: positive
(9) Attitude to oxygen: aerobic
(10) O-F test (by the Hugh Leifson method): F type (Fermentation)
(11) Acid formation from sugars
  positive: glucose, mannose, fructose, maltose, saccharose and trehalose;
  negative: arabinose, xylose, galactose, lactose, sorbitol, inositol and glycerine
(12) Growth pH range: pH 6.0–9.0
(13) Optimum growth temperature: 25°–37° C.

3. BE-3-3 strain

A. Morphology
(1) Form and size of cells: rod-shaped, 0.8–0.9×1.4–1.8 μm;
(2) Formation of spores: none
(3) Gram staining: negative B. Growth on various culture media (1) Bouillon-agar plate culture (28° C., 48 hours)
  ① Form of colony: rhizoid and lacerate
  ② Raising of colony surface: flat and smooth
  ③ Size: 5–9 mm
  ④ Color tone: pale grayish brown to bluish gray
(2) Bouillon-agar slant culture (28° C., 48 hours)
  ① Growth: good
  ② Form of growth: filiform
(3) Bouillon liquid culture (28° C., 48 hours)
  Growth: turbid throughout the entire liquid, sediment formed.
(4) Bouillon-gelatin stab culture (20° C., 6 days): not liquefied
(5) Litmus-milk culture medium (28° C., 4 days): substantially not changed C. Physiological properties:
(1) Reduction of nitrate (28° C., 5 days): no reductivity
(2) Formation of hydrogen sulfide (28° C., 5 days): formed
(3) Hydrolysis of starch: not hydrolyzed
(4) Catalase: positive
(5) Indole formation: not formed
(6) Ammonia formation from peptone and arginine: negative
(7) Methyl red test: negative
(8) V-P test: negative
(9) Attitude to oxygen: aerobic
(10) O-F test (by the Hugh Leifson method): O type (Oxidation)

(11) Acid formation from sugars
   positive: glucose, mannose, fructose and trehalose;
   negative: arabinose, xylose, galactose, maltose, saccharose, sorbitol, lactose, inositol and glycerine

(12) Growth pH range: pH 6.0–9.0

(13) Optimum growth temperature: 25°–37° C.

The above bacteriological properties were examined with reference to the taxonomical stnadards in Bergey's Manual of Determinative Bacteriology, 7th edition (1957). As the result, J-4 - 2 strain was identified to be a strain belonging to the genus Pseudomonas from the various properties such as being a straight short-rod bacterium, Gram-negative, having polar flagella, having no sporeforming ability, being oxidative of glucose, etc. and was designated as *Pseudomonas desmolytica* J-4-2. The AT-6-7 strain, which is a short-rod bacterium almost approximate to a coccus, Gram-positive, forms no filament and forms acids from carbchydrates, was identified to be a strain belonging to the genus Brevibacterium and designated as *Brevibacterium acetylicum* AT-6-7. The BE-3-3 strain, which is Gram-negative, forms acids from hexose, forms hydrogen sulfide with its cells being rod-shaped, was identified to belong to the genus Achromobacter and designated as *Achromobacter eurydice* BE-3-3.

The above three microorganism strains were identified according to Bergey's Manual of Bacteriology, 7th edition, and it is possible that they may belong to other species or genus when these strains are to be identified to belong to other species or genus according to different taxonomical standards due to some changes in taxonomical standards in the future. However, the microorganisms as designated above are inclusive of microorganisms which can at least produce nucleoside phosphorylase source in conformity with the object of the present invention and has the aforesaid bacteriological properties or bacteriological properties equivalent thereto, and can be unequivocally specified.

These three microorganism strains were deposited at the Fermentation Research Institute, Agency of Industrial Science & Technology on January 13, 1982, under the following deposition numbers (FERM P. No.). Further, these strains were sent directly from the Fermentation Research Institute to the American Type Culture Collection (ATCC), 12301 Parklawn Drive, Rockville, Md. U.S.A. for deposition, and deposited on Mar. 2, 1983, under the following deposition numbers (ATCC No.).

(1) *Pseudomonas desmolytica* J-4-2, FERM P-6307, ATCC 39311

(2) *Brevibacterium acetylicum* AT-6-7, FERM P-6305, ATCC 39311

(3) *Achromobacter eurydice* BE-3-3, FERM P-6304, ATCC 39312

The mutant strains derived from the above microorganism strains through induced mutation according to the mutagenic methods in general by a physical treatment such as irradiation of UV-ray, X-ray or γ-ray or a chemical treatment with nitroso-guanidine or other mutagens or natural mutation attributable to natural causes may be also available in the present invention, so long as they do not lose the ability to produce nucleoside phosphorylase source suitable for the object of the present invention.

Further, when the gene for nucleoside phosphorylase source suitable for the object of the present invention of the microorganism strains preferably used in the present invention as described above is integrated in a microorganism other than the genera Pseudomonas, Brevibacterium and Achromobacter if the characteristic of such a gene is phenotypically expressed, the method of employing the culture, the intact cells of such a microorganism or the modification thereof for the object of the present invention may also be included within the present invention.

In cultivation of these microorganisms to produce a nucleoside phosphorylase source, the culture medium and the method of culture employed are not particularly limited, so far as growth of these microorganisms is concerned.

As a culture medium, there may be employed one containing appropriate amounts of a carbon source and a nitrogen source assimilable by these microorganisms, optionally added with an inorganic salt, minute amounts of a growth promoter, defoaming agents, etc. More specifically, as carbon sources, there may be employed one or more of those selected suitably in view of assimilability by the microorganism employed from carbon sources in general, including sugars such as glucose, fructose, maltose, galactose, ribose, saccharose, starch, starch hydrolysate, molasses, waste molasses, etc. or derivatives thereof such as fatty acid esters thereof; natural carbohydrates such as wheat, wheat bran, rice, etc.; alcohols such as glycerol, mannitol, methanol, ethanol, etc.; fatty acids such as gluconic acid, pyruvic acid, acetic acid, citric acid, etc.; hydrocarbons such as normal paraffins, kerosene, etc.; amino acids such as glycine, glutamic acid, glutamine, alanine, asparagine, etc.; and so on. As nitrogen sources, there may be employed one or more of those selected suitably in view of assimilability by the microorganism employed from nitrogen sources in general, including organic nitrogenous materials such as meat extract (bouillon), peptone, yeast extract, dry yeast, soybean hydrolysate, soybean powder, milk casein, casamino acid, various amino acids, corn steep liquor, cotton seed meal or its hydrolysate, fish meal or its hydrolysate, hydrolysates of other animals, vegetables, microorganisms, etc.; inorganic nitrogen compounds such as ammonia, ammonium salts such as ammonium nitrate, ammonium sulfate, ammonium chloride, ammonium phosphate, ammonium carbonate, ammonium acetate and the like, nitric acid salts such as sodium nitrate, urea, and so on. Further, as inorganic salts, there may suitably be added one or more, in minute amounts, of phosphates, hydrochlorides, sulfates, carbonates, nitrates, acetates and others of magnesium, manganese, iron, zinc, copper, sodium, calcium, potassium, etc. If necessary, there may also be added a defoaming agent such as a vegetable oil or a surfactant, a minute amount of a growth promoter such as vitamins $B_1$, $B_2$, nicotinic acid, pantothenic acid, biotin, P-aminobenzoic acid, etc. When employing a microorganism exhibiting nutrient requirements, substances satisfying its growth must be added into the culture medium as a matter of course.

Cultivation may be performed in a liquid medium containing the above culture medium components by selecting a culture method suitable for the microorganism employed from conventional culture methods such as shaking culture, aerating stirring culture, stationary culture, continuous culture and others.

The cultural conditions may be suitably chosen depending on the microorganism and the culture medium employed, but generally by adjusting before start-up of cultivation at pH of about 6 to 8 and carrying out cultivation under the temperature condition of about 25° to 35° C. The culture duration may be a period sufficient for growth of the microorganism employed, being generally 1 to 3 days.

After culturing the microorganism as described above, the culture, the intact microbial cells collected from the culture according to a conventional method such as centrifugation, sedimentation separation, agglomeration separation, or a modification of microbial cells obtained by applying a suitable treatment on the living or intact cells may be used as the nucleoside phosphorylase source of the present invention. The "culture" herein refers to a product under the state where the culture medium and the cultured microbial cells after cultivation are still unseparated from each other. The "modification of cells" refers to dried microbial cells, microbial cells whose cell wall membrane having been modified, crushed microbial cells, immobilized microbial cells, extracts of microbial cells, protein fractions having nucleoside phosphorylase activity of extract of microbial cells or purified product thereof, immobilized product of the protein fractions or purified product thereof, and the like. Methods for obtaining the modification of microbial cells are to be illustrated below. Modifications of microbial cells can be obtained by applying on intact microbial cells singly or in combination physical treatment means such as freezing-thawing, lyophilization, air drying, acetone drying, heating under acidic or alkaline conditions, grinding, ultrasonic treatment, osmotic treatment, etc. or chemical or biochemical treatments such as enzymatic treatments with lysozyme, cell wall lysing enzymes, etc., contact treatments with solvents such as toluene, xylene, butyl alcohol or surfactants, or by applying on the extract of microbial cells singly or in combination enzyme separation and purification means such as salting-out, isoelectric precipitation, precipitation with organic solvents, various chromatographies, dialysis and others, or further by applying on intact microbial cells, extracts of microbial cells or purified products thereof an enzyme or cell immobilization means such as inclusion method, cross-linking method, adsorption method onto a carrier, etc.

Glycosylation or transglycosylation

The reaction in accordance with the present invention, namely enzymatic reaction of a guanine derivative of formula [I] with a 3-deoxyribose donor, which is glycosylation when the substituent R is hydrogen and is otherwise transglycosylation, is carried out by bringing a guanine derivative and a 3-deoxyribose donor into contact with the nucleoside phosphorylase source as described above in an aqueous medium. The kinds of the enzyme substrates are selected according to the kind of the enzyme source employed.

In a preferred embodiment of the present invention, there are two methods available to effect the contact.

The first method is one in which a guanine derivative and a 3-dioxyribose donor are caused to be present in the culture medium during cultivation of the aforesaid microorganism, thereby accumulating 3'-deoxyguanosine in the culture medium.

The above method may be carried out by adding necessary amounts of a guanine derivative and a 3-deoxyribese donor in the culture medium prior to cultivation and cultivating the microorganism therein, or by adding these substances at once at an appropriate period of time during cultivation, or by carrying out cultivation while adding intermittently or continuously these substances.

The second method may be carried out by bringing a culture, intact microbial cells or a modification of cells into contact with an aqueous medium containing a guanine derivative and a 3-deoxyribose donor under the conditions capable of forming 3'-deoxyguanosine.

An aqueous medium in which the contact between the reactants concerned is to take place may be water or various buffers preferred for enzymatic reactions (e.g. phosphate buffers, imidazole-hydrochloric acid buffer, veronal-hydrochloric acid buffer, Tris-hydrochloric acid buffer), which contains a phosphate ion generating source and may also contain various substances, if desired.

The enzymatic reaction of the present invention is mainly based on the action of phosphorylase, and therefore a phosphate ion must exist in the reaction system. In the case where a phosphate ion does not exist in the reaction system, an addition of a phosphate ion generating substance is necessary. As the phosphate ion generating substance, there may be employed any compound dissociable into phosphate ion in an aqueous medium, such as phosphoric acid itself, inorganic phosphoric acid salts such as salts of alkali metals, for example, sodium, potassium and the like, alkaline earth metals, for example, calcium, magnesium and the like or ammonium. These phosphate generating sources may be employed in amounts of about 1.0 to 2.5-fold moles per mole as phosphate ions per mole of the guanine derivative. As substances other than the phosphate ion generating source which may be contained in the aqueous medium, there may be employed sugars such as glucose, sacchrose and the like, organic solvents such as methanol, ethanol, propanol, butanol, pentanol, toluene, xylene, ethyl acetate and the like, various surfactants, metal salts and so on.

As the method to bring a nucleoside phosphorylase source into contact with a guanine derivative and a 3-deoxyribose donor in an aqueous medium, there may be employed the method in which the nucleoside phosphorylase source is suspended or dissolved in an aqueous medium containing these reaction substrates, optionally with stirring or shaking, or the method in which these reaction substrates are added at once, intermittently or continuously into a suspension or a solution of the nucleoside phosphorylase source in a reaction medium, or the method in which the nucleoside phosphorylase source is packed in a column optionally admixed with a suitable diluent or carrier or immobilized onto a membrane and an aqueous medium containing the reaction substrates is passed therethrough.

During the reaction, the substrate concentration is not particularly limited, and the reaction may be carried out under a suspended state of the substrates. But each reaction substrate is used usually at a concentration within the range from 5 to 50 mM, preferably about 15 to 35 mM for a guanine derivative and about 15 to 30 mM for 3-deoxyribose donor. The nucleoside phosphorylase source may be employed in an amount, which can easily be determined by those skilled in the art by considering the particular source material employed, the concentrations of the reaction substrates, the reaction efficiency and economy.

The reaction conditions, which are not particularly limited and may be determined while considering the optimum temperature and the optimum pH for the enzymatic action of the nucleoside phosphorylase source, stability of the substrates and reaction efficiency may generally comprise a temperature of 40° to 75° C., preferably 50° to 70° C. and a pH 5.0 to 9.0, preferably 6.0 to 8.0. When pH is changed during the reaction, an acid or an alkali can be used to correct the pH to a preferred level. When a nucleoside phosphorylase source derived from the aforesaid three microorganism strains of genera Pseudomonas, Brevibacterium and Achromobacter, the optimum temperature is around 50° to 70° C. and the reaction can be carried out at a relatively higher temperature, whereby there is the advantage that no countermeasure against microorganism contamination is required to be considered.

The reaction time, which may be determined while confirming the conversion of the reaction substrates to the desired product, may be generally about 15 to 45 hours, preferably 24 to 36 hours, in a batch system. In a columnar system, the reaction may be carried out under appropriate conditions set analogously as in the batch system.

After the enzymatic reaction, the nucleoside phosphorylase source may be removed by separation in a conventional manner, and the residual product is subjected to the step for isolation and purification of 3'-deoxyguanosine.

Isolation and purification of 3'-deoxyguanosine may be performed according to any of the methods known in the art by using separation/purification methods singly or in combination such as various chromatographies, for example, ion-exchange chromatography, adsorption chromatography, partition chromatography, gel filtration, etc., the counter-current partition method, the recrystallization method and others.

EXAMPLES OF THE PREFERRED EMBODIMENTS

The present invention is to be described in further detail below by referring to Examples, each of which is illustrative of an embodiment of the present invention and not limitative of the scope of the present invention. In Examples, analysis of 3'-deoxyguanosine was conducted by high performance liquid chromatography. When analyzed by means of the device and under the conditions shown below, 3'-deoxyguanosine is eluted at a retention time around 12.90 minutes and its quantity can be calculated from the calibration curve.

Device: Shimadzu High Performance Liquid Chromatograph LC-3A model (produced by Shimadzu Corporation)
Column: Sorbax ODS, 4.6 mm×250 mm (Shimadzu DuPont Co.)
Eluant: 20 mM Tris-hydrochloric acid buffer containing 5% acetonitrile (pH 7.5)
Flow rate: 1 ml/minute
Column operation temperature: room temperature

EXAMPLE 1

Two liters of a 2% bouillon culture medium were sterilized at 120° C. for 15 minutes and cooled. Then, 100 ml of a previously precultured culture broth of Brevibacterium acetylicum AT-6-7 (FERM P-6305) was added to the culture broth and cultivation was carried out at 28° C. for 22 hours.

After completion of the cultivation, the cells were collected by centrifugation and added into 200 ml of a sterilized water to be suspended therein. Into 200 ml of a substrate solution (pH 7.0) containing 25 mM GMP (disodium salt), 25 mM 3'-dAdo and 30 mM monosodium dihydrogen phosphate was added the above cell suspension and the reaction was carried out at 60° C. for 36 hours.

The reaction mixture after removal of the cells by centrifugation was analyzed by high performance liquid chromatography to show that the yield of 3'-deoxyguanosine was 36.58%. The yield of 3'-deoxyguanosine is defined as the molar ratio (%) of 3'-deoxyguanosine formed to 3'-deoxyadenosine added.

EXAMPLE 2

Cultivation was carried out in the same manner as in Example 1 except that Pseudomonas desmolytica J-4-2 (FERM P-6307) was used, and cells were collected and suspended in a sterilized water to obtain 200 ml of a cell suspension.

Into 200 ml of a substrate solution (pH 7.0) containing 25 mM Guo, 25 mM 3'-dAdo and 35 mM monopotassium dihydrogen phosphate was added the above cell suspension and the reaction was carried out at 60° C. for 36 hours. The cells were removed by centrifugation and the reaction mixture was analyzed to show that the yield of 3'-deoxyguanosine was 42.09%. The reaction mixture was diluted to one liter (pH 9.0), treated with an anion exchange resin "Diaion SA-12A" (trade name; produced by Mitsubishi Kasei Kogyo Co., Ltd.) (borate form) and the solution which had passed through the column and the water washings were combined and adsorbed on a cation exchange resin "Diaion PK-216" (trade name; produced by Mitsubishi Kasei Kogyo Co., Ltd.)(free acid form), followed by elution. The fractions of 3'-deoxyguanosine were neutralized, concentrated and cooled. The crude crystals precipitated were recrystallized from hot water to obtain 449 mg of 3'-deoxyguanosine crystals.

EXAMPLE 3

After cultivation of the same microorganism as in Example 2 conducted in the same manner except for using each 100 ml of a bouillon medium, cells were collected from each culture broth and 10 ml of a sterilized water was added to respective cells to prepare each cell suspension. To each of the suspensions was added each 10 ml of the solutions containing 20 mM 3'-dAdo, 25 mM monopotassium dihydrogen phosphate and 20 mM of the guanine derivative (Table 1 ), and the reaction was carried out at 60° C. for 24 hours. After the reaction, the supernatant obtained by centrifugation was analyzed to give the 3'-deoxyguanosine yield as shown in Table 1.

TABLE 1

| Guanine derivative | 3'-Deoxyguanosine yield (%) |
| --- | --- |
| Gua | 2.14 |
| Guo | 26.36 |
| GMP | 21.72 |

When the same experiments were performed for Brevibacterium acetylicum AT-6-7 (FERM P-6305) and Achromobacter euridice BE-3-3 (FERM P-6304), the similar results as shown above were obtained with respect to the reactivities for guanine derivatives.

EXAMPLE 4

Example 3 was repeated by use of Brevibacterium acetylicum AT-6-7 (FERM P-6305) as the nucleoside phosphorylase source, GMP as the guanine derivative and the respective enzymatic reaction temperatures of 40° to 80° C. (Table 2), under otherwise the same conditions as in Example 3, and 3'-deoxyguanosines formed were analyzed to give the results as shown in Table 2.

TABLE 2

| Reaction temperature | 3'-Deoxyguanosine yield (%) |
|---|---|
| 40° C. | 5.81 |
| 50° C. | 12.32 |
| 60° C. | 20.86 |
| 70° C. | 4.32 |
| 80° C. | 0 |

When the same experiments were performed for the BE-3-3 strain (FERM P-6304) and the J-4-2 strain (FERM P-6307), substantially the similar results were obtained with respect to the effect of the reaction temperature.

EXAMPLE 5

Example 3 was repeated by use of *Achromobacter euridice* BE-3-3 (FERM P-6304) as the nucleoside phosphorylase source, GMP as the guanine derivative and the respective enzymatic reaction pH's of 6.0 to 9.0 (Table 2 ), under otherwise the same conditions as in Example 3 , and 3'-deoxyguanosines formed were analyzed to give the results as shown in Table 3.

TABLE 3

| Reaction pH | 3'-Deoxyguanosine yield (%) |
|---|---|
| 6.0 | 19.70 |
| 7.0 | 21.26 |
| 8.0 | 19.46 |
| 9.0 | 11.28 |

When the same experiments were performed for the AT-6-7 strain (FERM P-6305) and the J-4-2 strain (FERM P-6307), substantially the similar results were obtained with respect to the effect of pH.

EXAMPLE 6

After cultivation was carried out in the same manner as in Example 1 by use of the same nucleoside phosphorylase source as in Example 5, the cells were collected and suspended in a sterilized water to obtain each 1 ml of cell suspensions. As the substrate solutions, there were prepared various combinations of aqueous solutions (pH 7.0) containing as a 3-deoxyribose donor 15 mM of 3'-dAdo, 3'-dAMP or 3'-dIno, as a guanine derivative 15 mM of GMP, GDP, GTP, 2'-dGuo or 2'-dGMP and 20 mM of monopotassium phosphate. Such cell suspensions and substrate solutions were mixed, respectively, and the reactions conducted at 60° C. for 24 hours. As the result, the yields of 3'-deoxyguanosine obtained were as shown in Table 4.

TABLE 4

| Substrate solution | | 3'-deoxy- |
|---|---|---|
| 3'-Deoxyribose donor | Guanine derivative | guanosine yield (%) |
| 3'-dAdo | GMP | 62.70 |
| 3'-dAdo | GDP | 56.02 |
| 3'-dAdo | GTP | 14.87 |
| 3'-dAdo | 2'-dGuo | 43.82 |
| 3'-dAdo | 2'-dGMP | 34.50 |
| 3'-dAMP | GMP | 63.48 |
| 3'-dAMP | GDP | 44.74 |
| 3'-dAMP | GTP | 7.66 |
| 3'-dAMP | 2'-dGuo | 27.30 |
| 3'-dAMP | 2'-dGMP | 24.64 |
| 3'-dIno | GMP | 31.04 |

What is claimed is:

1. A microbiologically pure culture of a microorganism of *Brevibacterium acetylicum* AT-6-7, ATCC 39311 or a mutant thereof which has a nucleoside phosphorylase activity.

2. The microbiologically pure culture of a microorganism as claimed in claim 1 which is *Brevibacterium acetylicum* AT-6-7, ATCC 39311.

3. The microbiologically pure culture of a microorganism as claimed in claim 9 in which the mutant is derived from the induced mutation or spontaneous mutation of *Brevibacterium acetylicum* AT-6-7 , ATCC 39311 and which has a nucleoside phosphorylase activity.

* * * * *